United States Patent [19]

Odell

[11] Patent Number: 4,739,045

[45] Date of Patent: Apr. 19, 1988

[54] PROCESS FOR THE DISSOLUTION OF NUCLEOTIDES AND POLYNUCLEOTIDES

[75] Inventor: Barbara Odell, Gillingham, England

[73] Assignee: Shell Oil Company, Houston, Tex.

[21] Appl. No.: 708,622

[22] Filed: Mar. 5, 1985

[30] Foreign Application Priority Data

Mar. 6, 1984 [GB] United Kingdom ................ 8405763

[51] Int. Cl.$^4$ ...................... A61K 31/70; C07H 19/10
[52] U.S. Cl. ........................................ 536/29; 536/27; 536/28
[58] Field of Search ............................ 536/27, 282, 29

[56] References Cited

U.S. PATENT DOCUMENTS 3,433,782  3/1969  Kreiser .................................. 536/27

OTHER PUBLICATIONS

Pitha et al, *Biochimica et Biophysica Acta*, 425, (1976) 287-295.
Bose et al, *J. Org. Chem.*, 48, (1983) 1780-1782.
Smid, *Pure and Applied Chem.*, 54, (1982) 2129-2140.

*Primary Examiner*—J. R. Brown
*Assistant Examiner*—L. Eric Crane

[57] ABSTRACT

Process for the dissolution of nucleotides and polynucleotides in non-aqueous solvents and mixed non-aqueous solvent systems using macromolecular ligands, solutions thereby obtained and their use for the separation and purification of DNA, e.g. for RNA and protein, in the chemical synthesis of DNA, in the conversion of double stranded DNA into single stranded DNA, and in the chemical modification of DNA.

8 Claims, No Drawings

PROCESS FOR THE DISSOLUTION OF NUCLEOTIDES AND POLYNUCLEOTIDES

FIELD OF THE INVENTION

The present invention relates to a process for the dissolution of nucleotides and polynucleotides and derivatives thereof in non-aqueous solvents and mixed non-aqueous/aqueous solvent systems. In particular the invention relates to the dissolution in such solvents or solvent systems of polynucleotides such as the nucleic acid deoxyribonucleic acid (DNA) and salts thereof. The invention further relates to the separation of DNA from ribonucleic acid (RNA) and extraneous protein and to the separation of various DNA mixtures.

BACKGROUND OF THE INVENTION

Applicants have tried to dissolve DNA in non-aqueous solvents like methanol, ethanol, and organic solvent mixtures like methanol/ethyl acetate, methanol/chloroform, and methanol/toluene but in all cases the DNA appeared not to dissolve.

However it has now been found that DNA whether it is in double-helical or single-stranded form can be successfully dissolved in the above solvents or mixed aqueous/non-aqueous solvent systems if one adds to the solvent certain macromolecular ligands such as crown ethers and cryptands which belong to the group of macrocyclic receptor molecules.

SUMMARY OF THE INVENTION

Therefore the present invention provides a process for the dissolution of nucleotides and/or polynucleotides and/or derivatives thereof in a non-aqueous and/or mixed non-aqueous medium in the presence of a macromolecular ligand or a mixture of macromolecular ligands.

Preferably the weight ratio of macromolecular ligand:nucleotide or polynucleotide is in the range of 1-500:1. The molar ratio of macromolecular ligand:polynucleotide is then in the range of $10^3$-$10^6$:1 whereas the molar ratio of macromolecular ligand:polynucleotide is then in the range of 1-100:1.

A crown-ether is a highly selective complexing agent which can form complexes with metal ions like alkali and alkaline earth cations, ammonium and alkylammonium cations via electrostatic and hydrogen bonding interactions. From J. Chem. Soc. Perkin Trans. I, 1982 pp. 2359-2363, several types of crown-ethers are known with either oxygen, nitrogen, or sulphur donor atoms. Also a number of oxygen, nitrogen and/or sulphur donor atoms-containing macropolycyclic compounds such as macrobicyclic compounds are known from J. M. Lehn et al, J. Am. Chem. Soc., 1981, pp. 1282-1283. In this article the complexation of certain nucleotide phosphate polyanions by macrocyclic polyammonium structures in aqueous solutions is described. The above macropolycyclic compounds may also be suitably used in the present process.

The association between polycrown ethers and polynucleotides in the presence and absence of cations has been reported in aqueous solution from J. Pitha and J. Smid, Biochimica et Biophysica Acta, 1976, 425,287 and J. Smid, Pure and Appl. Chem., 1982, 54,2129.

Crown-ethers and macropolyclic compounds which are preferably used in the present process are selected from the group consisting of 18-crown-6, 15-crown-5, dibenzo-18-crown-6, dicyclohexyl-18-crown-6, 21-crown-7 and cryptand [222].

Nucleotides and DNA may be dissolved in polar non-aqueous solvents such as lower alkanols, e.g. methanol, ethanol and the like, dimethylsulphoxide and the like. The non-aqueous medium may be, or be further diluted with, a non-polar solvent such as dichloromethane, ethyl acetate, acetone, diethyl ether, chloroform, tetrahydrofuran, toluene and the like.

It appeared that, both free acid and metal salt (particularly sodium salt) forms of nucleotides and polynucleotides such as DNA can easily be dissolved in non-aqueous solvent systems using the process according to the present invention. Therefore these forms are preferred. Preferably a substantial amount of the macromolecular ligands have been attached to organic or inorganic support materials. The present invention further provides a non-aqueous or mixed non-aqueous solution comprising one or more nucleotide macromolecular ligand complexes and/or polynucleotide macromolecular ligand complexes which solutions have been obtained by the present process. The present invention still further provides a non-aqueous/aqueous solution comprising one or more nucleotide macromolecular ligand complexes and/or polynucleotide macromolecular ligand complexes per se.

As will be appreciated the present invention offers a whole range of possible applications in the field of biotechnology, biochemistry and genetic engineering especially for those applications for which it is essential that nucleotides and/or polynucleotides (especially DNA) can be selectively dissolved in non-aqueous and mixed non-aqueous/aqueous solvents. It has been found that the available DNA preparations are much more soluble in organic solvents comprising crown ethers and/or macropolyclic compounds than RNA preparations. Thus the purification of DNA from RNA and from extraneous protein can be carried out very simply by selective dissolution in an alcohol, e.g. a lower alkanol, containing a macrocyclic polyether in which medium the less soluble components such as RNA and protein precipitate. Therefore the present invention also provides a use of the present process for the separation and purification of nucleotides and polynucleotides, in particular the separation and purification of DNA from RNA and protein and the separation of mixtures of DNA's. Further preferred uses of the present process are described hereafter. The fractional crystallisation of nucleotides and polynucleotides such as DNA and the employment of crown ethers and/or macropolycyclic compounds attached to organic polymers or inorganic supports such as silica-alumina offer additional purification methods (e.g. chromatography) that are not readily available using conventional techniques. Other applications may be found in the synthesis of nucleotides such as DNA, where chemical routes can thus be carried out in non-aqueous solvents or non-aqueous/aqueous solvent systems.

The invention may further be used for the conversion of double stranded DNA into single stranded DNA as it appears that the UV/visible spectra of DNA (1 mg/10 ml) solutions in various solvent systems (e.g. water/methanol with crown ether, and methanol/dichloromethane with crown ether) all exhibited an increase in absorbance of about 30-40% as well as an additional shoulder at about 270 nm whereas no shoulder is present when water is used as solvent.

The increase in absorbance is consistent with single stranded denatured DNA and indeed the spectrum of single stranded DNA in methanol/crown ether mixtures exhibited similar absorbance values to water solutions of single stranded DNA. Renatured double-helical DNA can be retrieved upon dialysis of the methanol/crown ether mixture into water as evidenced by absorbance measurements at 260 nm.

The above use opens the possibility of carrying out chemical modifications of DNA with e.g. chemical reagents which are particularly moisture sensitive such as alkylating reagents.

The resulting DNA molecule can be reclaimed into water by, for example, dialysis and gel filtration techniques. Such handlings of DNA in non-aqueous solvents may be of use to studies involving carcinogenesis.

ILLUSTRATIVE EMBODIMENTS

The invention will now be further described with reference to the following Example. In this example set forth in Table I and II, effectiveness of the present dissolution process is shown but also its selectivity towards different nucleotides and polynucleotides which, as indicated before, makes the present process very useful for, inter alia, the separation and purification of nucleotides and polynucleotides.

EXAMPLE

The Dissolution of Nucleotides and Polynucleotides (eg DNA in MeOH with Crown Ether (18-C-6))

TABLE 1

| Nucleotide (mgs) | MeOH (volume) | CE (18C6) mgs | Weight ratio Nucleotide:CE |
|---|---|---|---|
| cytosine 5'monophosphate COMP 3.7 mg | 2 ml | >500 mg | in* |
| 2-adenylate 5'monophosphate AMP (acid) 21.5 mg | 4 ml | >500 mg | in* |
| 2-guanylate monophosphate GMP Na salt | | | |
| 24.3 mg | 2 ml | 660 mg | 1:27 (1:42)** |
| 1.2 mg | 2 ml | 145 mg | 1:120 (1:182)** |
| Thymidine 5'-monophosphate TMP acid | | | |
| 13.4 mg | 2 ml | 40.3 mg | 1:3 (1:3.9)** |
| 2-deoxyadenylate monophosphate | | — | dissolves without CE |
| d AMP acid 14.9 mg | 2 ml | | |
| Uridine 5'monophosphate | 2 ml | — | dissolves without CE |
| UMP 6.5 mg | | | |

*insoluble
**molar ratio
CE = crown ether

TABLE 2

| DNA or RNA | (ml of MeOH) | 18C6 (mg) | Weight ratio of polynucleotide:CE |
|---|---|---|---|
| DNA (micrococcus lysodeikticus) Type XI | | | |
| 3.1 mg | 3-5 ml | 175 mg | 1:56 |
| 1.4 mg | 2 ml | 50.3 mg | 1:36 |
| 1.0 mg | 2 ml | cryptand [222] 50.0 mg | 1:50 |
| Double-Helix acid DNA (single strand) Calf Thymus | | | |
| 3.7 mg | 2 ml | 204 mg | 1:55 |
| acid 1.5 mg | 2 ml | cryptand [222] 60.0 mg | 1:40 |
| DNA Type 1 Calf Thymus Na Salt | | | very soluble with CE |
| 3.4 mg | 2 ml | 97.3 mg | 1:28.5 |
| DNA Type V | | | very soluble with CE |
| Calf Thymus 4.2 mg | 2 ml | 77.8 | 1:18.5 |
| DNA Type III Salmon testes Na Salt | | | |
| 4.1 mg | 3 ml | 408 mg | 1:100 |
| 1.8 mg | 2 ml | 80 mg | 1:44 |
| DNA Type IV (Herring sperm degraded free acid) | | | |
| 19.0 mg | 4 ml | 1.3 g | in* |
| DNA Type VIII 4.3 mg from *Eschericha Coli* | 4 ml | 103.0 mg | 1:24 very soluble |
| DNA (Type I) Calf Thymus Na Salt | | | |
| 2.6 mg | 2 ml | 58 mg | 1:22 |
| RNA (calf liver) 3.9 ml | 2 ml | 364 mg | in* |
| RNA (calf liver) Type IV | | | |
| 6.1 mg | 4 ml | >500 mg | in* |
| RNA (bakers yeast) 7.0 mg | 4 ml | >500 mg | in* |
| RNA (Torula yeast) Type VI 3.4 mg | 4 ml | >700 mg | in* |

All the nucleotides and polynucleotides mentioned in the tables are available from Sigma Chemical Company (Ref. Sigma Chemical Company Catalogue on biochemical and organic chemical compounds, February, 1984.)

Crown ether (cryptand) alcoholic solutions of DNA remain homogeneous on addition of non-polar solvents such as dichloromethane, chloroform, ethyl acetate, toluene diethylether, tetrahydrofuran etc [in concentrations of up to 95% non-polar solvent, 5% methanol].

What is claimed is:

1. A process for the dissolution of DNA polynucleotides in a non-aqueous medium which consists of treating DNA polynucleotides with a non-aqueous medium in the presence of a macromolecular ligand or a mixture of macromolecular ligands to obtain a solution of solubilized DNA polynucleotides in the medium.

2. A process according to claim 1 in which the weight ratio of macromolecular ligand:polynucleotide is in the range of 1–500:1.

3. A process according to claim 2 in which the macromolecular ligand is selected from the group consisting of 18-crown-6, 15-crown-5, dibenzo-18-crown-6, dicyclohexyl-18-crown-6, 21-crown-7, and cryptand [222].

4. A process according to claim 1 in which the non-aqueous medium is a solvent selected from the group consisting of methanol, ethanol or dimethylsulphoxide or a mixture of these solvents with dichloromethane, chloroform, ethyl acetate, acetone, toluene, diethyl ether and tetrahydrofuran.

5. A process according to claim 4 wherein the solvent is methanol.

6. A process according to claim 1 in which the polynucleotides are in the form of the free acid or its salt.

7. A process according to claim 1 in which a substantial amount of the macromolecular ligands had been attached to organic or inorganic support materials.

8. A process in which double-stranded DNA is converted into single-stranded DNA which consists of treating double-stranded DNA with a non-aqueous medium in the presence of a macromolecular ligand or a mixture of macromolecular ligands and recovering the single-stranded DNA as a solution in the medium.

* * * * *